(12) United States Patent
Girndt

(10) Patent No.: US 8,931,344 B2
(45) Date of Patent: Jan. 13, 2015

(54) METHOD AND APPARATUS FOR INSPECTING FLAWS IN OIL FIELD TUBULARS

(76) Inventor: Richard J. Girndt, Spring, TX (US)

( * ) Notice: Subject to any disclaimer, the term of this patent is extended or adjusted under 35 U.S.C. 154(b) by 413 days.

(21) Appl. No.: 13/016,688

(22) Filed: Jan. 28, 2011

(65) Prior Publication Data

US 2011/0219881 A1 Sep. 15, 2011

Related U.S. Application Data

(60) Provisional application No. 61/299,213, filed on Jan. 28, 2010.

(51) Int. Cl.
*G01N 29/04* (2006.01)
*G01N 29/06* (2006.01)
*G01N 29/22* (2006.01)

(52) U.S. Cl.
CPC ...... *G01N 29/225* (2013.01); *G01N 2291/2634* (2013.01); *G01N 29/069* (2013.01)
USPC .............................................. 73/622; 73/628

(58) Field of Classification Search
USPC ............................ 73/622, 625, 628, 637, 638
See application file for complete search history.

(56) References Cited

U.S. PATENT DOCUMENTS

| 5,175,964 | A | | 1/1993 | Girndt | |
|---|---|---|---|---|---|
| 5,600,069 | A | | 2/1997 | Girndt et al. | |
| 5,684,252 | A | * | 11/1997 | Kessler et al. | 73/618 |
| 6,945,113 | B2 | * | 9/2005 | Siverling et al. | 73/622 |
| 7,140,253 | B2 | * | 11/2006 | Merki et al. | 73/620 |
| 7,293,461 | B1 | | 11/2007 | Girndt | |
| 7,401,518 | B2 | * | 7/2008 | Sfeir et al. | 73/602 |
| 7,552,640 | B2 | * | 6/2009 | Sfeir et al. | 73/602 |
| 7,578,166 | B2 | * | 8/2009 | Ethridge et al. | 73/1.82 |
| 7,581,444 | B2 | * | 9/2009 | Maurer et al. | 73/597 |
| 8,061,208 | B2 | * | 11/2011 | Roberts et al. | 73/622 |
| 8,214,161 | B2 | | 7/2012 | Girndt | |
| 2008/0178678 | A1 | | 7/2008 | Girndt | |

* cited by examiner

*Primary Examiner* — J M Saint Surin
(74) *Attorney, Agent, or Firm* — Fulbright & Jaworski LLP

(57) ABSTRACT

Methods and apparatus for inspecting a flaws in tubular disclosed herein include but are not limited to inspection stations comprising one or more chutes adapted to receive a tubular, an inspection assembly adapted to ultrasonically inspect a tubular in the one or more chutes, and one or more rotators for apply directional forces on the tubular to advance and rotate the tubular in the one or more chutes. The inspection assembly is adapted to ultrasonically inspect tubulars while the tubulars are under a rotational force in the chute. The inspection assembly may be further adapted to identify the end of a tubular in a first chute and index the position of the inspection assembly over a second chute to inspect a tubular loaded in the second chute.

18 Claims, 4 Drawing Sheets

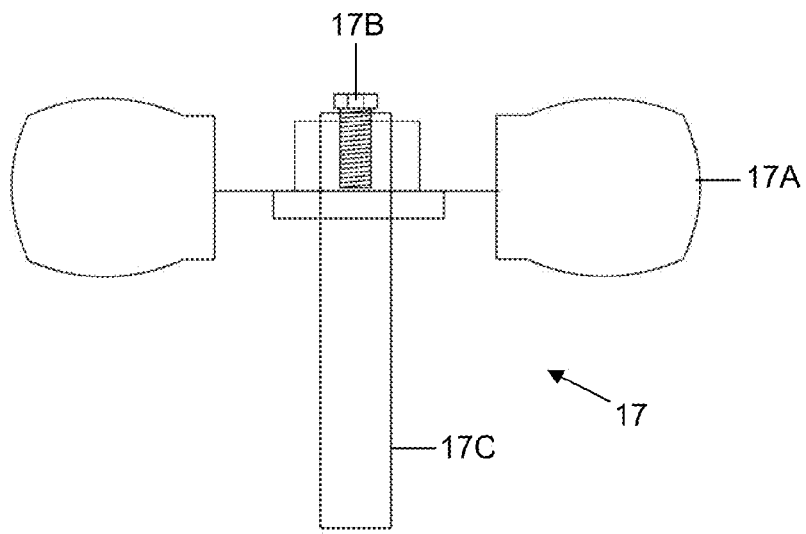
FIG. 2A (side view)
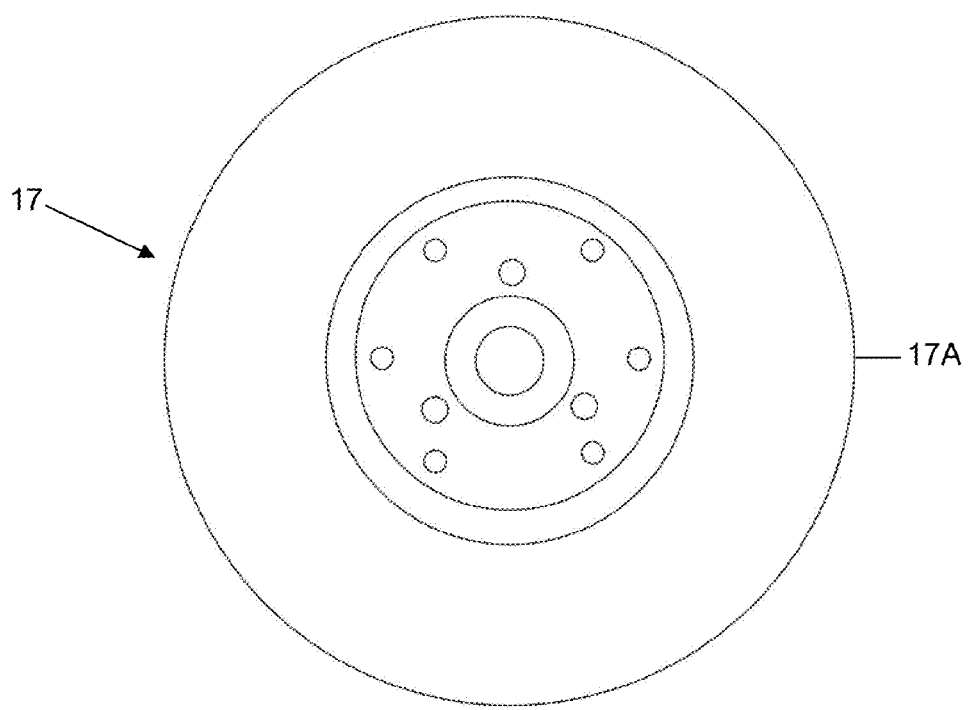
FIG. 2B (overhead view)

METHOD AND APPARATUS FOR INSPECTING FLAWS IN OIL FIELD TUBULARS

RELATED APPLICATIONS

This application claims priority to U.S. Provisional Patent Application No. 61/299,213 filed Jan. 28, 2010, which is hereby incorporated by reference in its entirety.

TECHNICAL FIELD

The present invention relates to methods and apparatus for inspecting flaws in tubulars, and more particularly to methods and apparatus for ultrasonic inspection of tubulars used in the oil field industry.

BRIEF SUMMARY OF THE INVENTION

The method and apparatus for inspecting flaws in oil field tubulars includes an inspection station (10) and an inspection assembly (20). The inspection station (10) preferably comprises a first chute (11A) and second chute (11B), third chute (11C) and fourth chute (11D) for holding and spinning oil field tubulars (pipes) as the tubular is inspected by the inspection assembly (20). The inspection station's first chute (11A) and second chute (11B) are preferably positioned side-by-side (parallel), as are third chute (11C) and fourth chute (11D). First and second chutes (11A, 11B) preferably align end-to-end with third and fourth chutes (11C, 11D) such that chutes (11A, 11B) make up the length of one side of the inspection station and chutes (11C, 11D) make up the other side. Two pipe stops (17), one between first chute (11A) and third chute (11C) and one between second chute (11B) and fourth chute (11D), preferably divide the inspection station's two sides at its approximate midpoint.

Each chute (11A-D) preferably includes one or more rotators (15) which rotate to spin a tubular circumferentially. The rotators (15) apply one or more directional forces on the tubular that cause the tubular to walk/move toward the middle of the inspection station against pipe stop (17) as the tubular spins. Walking force is applied to the tubular by rotators (15) by canting or skewing the rotators (15), elevating the end of the tubular opposite the pipe stop (17), or another manner that tends to cause a spinning tubular to move along chutes in the inspection station and toward and/or against pipe stop (17). Optionally, the rotators (15) apply a rotational force on the tublars by positioning the rotators to spin in a transverse direction across the tubular. Rotators (15) may also apply a combination of rotational and walking forces on the tubular to generate the desired amount of spinning and advancing action of the tubular. The pipe stop (17) between chutes (11A, 11C) and the pipe stop (17) between chutes (11B, 11D) provide a counter force to the walking force applied on tubulars that tends to hold the tubular in the chute as it spins. The combination of the counter force from the pipe stop (17) and walking force and/or rotational force from the rotators enable a tubular spinning in a chute to maintain its position in the chute, and at the same time maintain a relative position with tubulars spinning in others chutes of the inspection station (10). The preferred distance between spinning tubulars on either side of a pipe stop (17) is the diameter of the pipe stop (17). The inspection station (10) thus provides an efficient means for advancing a tubulars into position within its chute and spinning tubulars in a place in the chutes. The station (10) also provides a unique mechanism for rotating more than one tubular in proximity with each other, so that the tubulars may be ultrasonically inspected by the inspection assembly (20).

The inspection station preferably includes a frame assembly (12). The frame assembly (12) is formed with a first rail (13) and a second rail (14) which are positioned around the perimeter of the inspection station (10). Frame supports (16) are positioned on opposite ends of the station to provide structural support to the frame assembly, its member parts, and the overhead head inspection assembly traveling thereon.

Inspection assembly (20) traverses along rails (13 and 14) when performing ultrasonic flaw inspections on tubular loaded into the station. The inspection assembly (20) comprises a carriage (21) for positioning and repositioning a plurality of ultrasonic transducers. The transducers are operable to ultrasonically inspect for longitudinal, transverse, wall thickness, oblique, and other flaws in tubulars. The carriage (21) includes at least one longitudinal support member (22), lateral support member (23), and hydraulic or air cylinder (not shown). The support members and cylinder work together to support and maneuver the transducers (24) into position as they inspect tubulars loaded in the chutes. The cylinder and support members are adapted to move the transducers to a position over the tubular in any of the chutes during inspection. Optionally, a positioning sensor (25) is installed on the carriage to provide positioning data for the inspection assembly (20). The positioning sensor utilizes photo cell, infrared, or equivalent technology for identifying and reporting the position of the inspection assembly, carriage, transducers, and/or tubulars as needed.

In one embodiment, an apparatus for inspecting a tubular including at least one chute adapted to receive a tubular, an inspection assembly adapted to ultrasonically inspect a tubular in the chute, and at least one rotator adapted to apply a force on the tubular within the chute so that the inspection assembly can ultrasonically inspect the tubular. Optionally, the inspection assembly is adapted to ultrasonically inspect the tubular while the tubular is under a rotational force. It may also be adapted to ultrasonically inspect the tubular while the tubular is under a walking force. The inspection assembly is also optionally adapted to ultrasonically inspect the tubular while the tubular is under a walking force and a rotational force.

In another embodiment, the inspection assembly comprises a pipe stop for applying a counter force on the tubular while the tubular is under a walking and/or the rotational force, wherein the combination of the counter force and the walking force and/or rotational force maintain the tubular in the chute. A plurality of chutes adapted to receive tubulars and a plurality of rotators adapted to apply a force on said tubular may also be installed. The inspection assembly may also include a plurality of pipe stops for applying a counter force on tubulars while said tubulars are under a walking force and/or rotational force; wherein the combination of said counter force and said walking force or rotational force maintain said tubular in the chute. Optionally, the inspection assembly may comprise one or more ultrasonic transducers adapted to detect flaws in a tubular while the tubular is under a force applied by the rotator. The inspection assembly may also be adapted to pass over the chutes while inspecting tubulars loaded in the chute for flaws.

Another embodiment is formed of an apparatus for inspecting flaws in tubular comprising: an inspection assembly; one or more transducers connected to the inspection assembly, wherein the transducers are operable to ultrasonically inspect for flaws in a tubular under a walking and/or rotational force; wherein the inspection assembly is operable to traverse upon a support frame while the transducers inspect the tubular for flaws. Optionally, the inspection assembly comprises a carriage for positioning and repositioning the transducers relative to the tubular, and or a sensor operable to communicate with the carriage. The sensors are operable to identify the position of a tubular and/or flaws in the tubular. Alternatively, the positioning sensor is operable to report the position of the inspection assembly, carriage, transducers and/or tubular while the inspection assembly detects flaws in the tubular under the walking/or rotational force.

In yet another embodiment, a method for detecting flaws in oil field tubulars comprises applying at least one force on the tubular to induce movement of the tubular; positioning an ultrasonic transducer relative to the tubular; inspecting the tubular for flaws while the tubular is under the at least one force; and reporting the position of any flaws detected in the tubular. In this method, the force may be a walking force and/or rotational force. Such forces maintain the position of the tubular in the chute. The method can also include positioning the ultrasonic transducer comprises traversing the ultrasonic transducers over the tubular while the tubular is under the force. Reporting comprises identifying the location of the end of a tubular in a first chute and the location of the end of a tubular in a second chute. Inspecting comprises indexing the position of an inspection assembly from a first chute to an second chute upon detecting the end of a tubular in the first chute.

The foregoing has broadly outlined certain objectives, features, and technical advantages of the present invention in order that the detailed description of the invention that follows may be better understood. Additional features and advantages of the invention are described hereinafter, and form the subject of certain claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages are better understood from the following description when considered in connection with the accompanying figures. It is to be expressly understood, however, that such description and figures are provided for the purpose of illustration and description only and are not intended as a definition of the limits of the present invention.

BRIEF DESCRIPTION OF THE DRAWINGS

FIGS. 2A and 2B are example embodiments of the pipe stops;

DETAILED DESCRIPTION OF THE INVENTION

Figure 1:
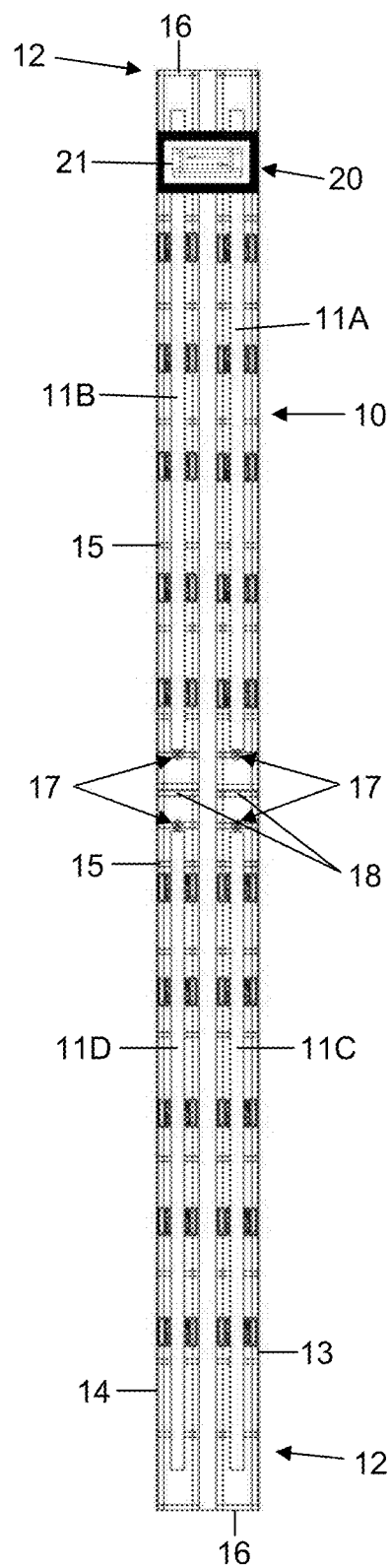
FIG. 1 is an example embodiment of the inspection station and inspection assembly.

FIG. 1 shows the inspection station (10). The inspection station includes a plurality of chutes for holding tubulars while they are inspected by the inspection assembly. In the preferred embodiment, the inspection assembly includes a first chute (11A), second chute (11B), third chute (11C), and fourth chute (11D) (each, a "chute (11)"). Additional or fewer chutes are also envisioned; however, the inspection station (10) preferably includes an equal number of chutes on each side. The chutes are long enough to accommodate at least one tubulars ranging in length from 20 feet to 50 feet, and wide enough to accommodate tubulars ranging diameter from 2⅜ inches to 20 inches. Longer and shorter chutes, as well as wider and more narrow chutes are also envisioned to accommodate all shapes of tubulars used in oil fields, or other industries that require high speed ultrasonic scanning.

Each chute (11) is preferably fitted with at least one rotator (15) for spinning tubulars loaded in the chute. Rotators (15) are adapted to spin tubulars about their longitudinal axis and, at the same time, apply a walking force on the tubular propelling it toward the middle of the inspection station (10) and against pipe stop (17). The pipe stop (17) is positioned at the end of each chute to prevent the tubular from traveling out of the chute and inspection area. Rotators (15) are preferably formed with a cone shaped channel at their middle point to hold tubulars of varying diameter using gravity. Rotators of flat, round, and other shapes are also envisioned. Rotators are preferably cocked, or positioned at an appropriate angle with respect to the tubular, to generate axial spin on the tubular and the walking force that tends to propel the tubular inward on the station. A divider (18) is preferably included on the inspection station (10) at or near the pipe stops, about the mid point of the station (10). The divider separates the pipe chutes on the upper half of the inspection from the pipe chutes on the lower half of the station. The divider may also provide a center support for the inspection assembly. The divider optionally also supports ultrasonic instrumentation or pulsers, which are optimally located equidistant from the ends of pipe chutes.

As an alternative to rotators (15), inspection station (10) is fitted with chucks (not shown) for rotating tubulars. Chucks couple with the outside or inside surface of the ends of a tubular to rotate the tubular along its longitudinal axis. Chucks are positioned to hold the tubular within the working area of the chute as it spins. Chucks are traditionally used in threading oil field tubulars. However, when installed on inspection station (10), chucks provide a means for spinning tubulars in place as needed in the disclosed embodiments.

The installation station includes a frame assembly (12). The frame assembly (12) structurally supports the chutes (11), rotators (15), pipe stops (17), and tubulars loaded into the inspection station (10). The frame assembly (12) includes frame supports (16) that attach to the above mentioned member parts of the inspection station, and to load bearing portions of the frame to provide structural integrity. Divider (18) also attaches to the frame assembly (12) and provides load bearing support. The frame assembly (12) is preferably approximately 100 feet in length or a length sufficient to accommodate two chutes positioned end-to-end, each loaded with the longest oil field tubular available. FIG. 1 shows a first chute (11A) and second chute (11C) positioned end-to-end, and third chute (11B) and fourth chute (11D) positioned end-to-end, respectively. Frame assemblies (12) of shorter and longer lengths are also envisioned. At least part of the frame assembly (12) preferably defines the perimeter of the inspection station and supports an inspection assembly (20) to travel thereon. Divider (18) includes vertical structural beams to support the weight of frame assembly (12) and rail (14). A The frame assembly (12) includes a first rail (13) and a second rail (14) to support the inspection assembly (20) as it travels. During tubular inspections, the inspection assembly (20) moves back and forth along the rails (13 and 14), passing over the top of the chutes (11) and any tubulars (50) loaded therein. Rails (13 and 14) preferably run the entire length of the inspection station, or at least long enough to enable the inspection assembly (20) to pass over and ultrasonically inspect tubulars loaded in the chutes. Frame supports (16) are attached to rails (13 and 14) and accommodate the rails' load bearing requirements.

FIGS. 2A and 2B show the pipe stop (17). Pipe stop (17) is positioned to contact the end of a tubular spinning with chute (11). Pipe stop (17) is preferably rigidly attached to frame assembly (12), divider (18), and/or structural supports of the inspection assembly (10). Alternatively, movable pipe stops are also envisioned to position and reposition the stop as needed. In preferred embodiments, pipe stop (17) contacts tubulars in end-to-end chutes, such as chutes (11A, 11C) or (11B, 11D), allowing tubulars in chutes on opposite sides of pipe stop (17) to spin in place. Alternatively, more that one pipe stop may be positioned between end-to-end chutes.

FIG. 2A shows a side view of pipe stop (17). Circular member (17A) rotates on and is supported by upright support member (17C). Coupling member (17B) secures circular member (17A) to upright support member (17C). Upright member extends from frame assembly (12) to up to an elevation where circular member (17A) may contact tubulars spinning in the chutes.

FIG. 2B shows and over head view of pipe stop (17). Circular member (17A) may be constructed of rubber, a frictionless material, or any other composition that enables contacting tubulars to spin in a non-destructive manner.

Figure 3A:
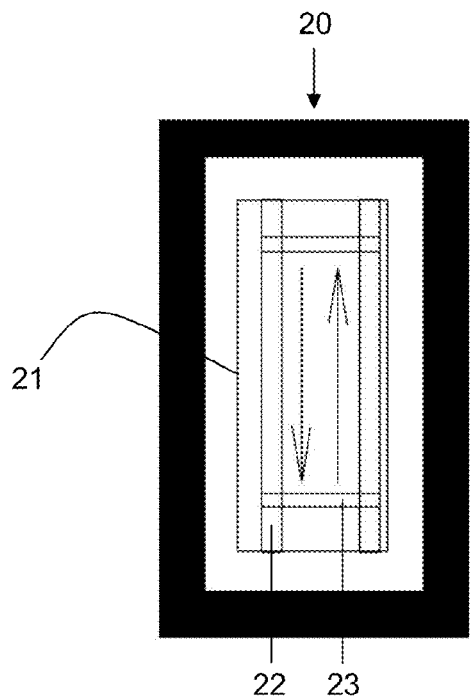
FIGS. 3A and 3B are example embodiments of the inspection assembly.
Figure 3B:
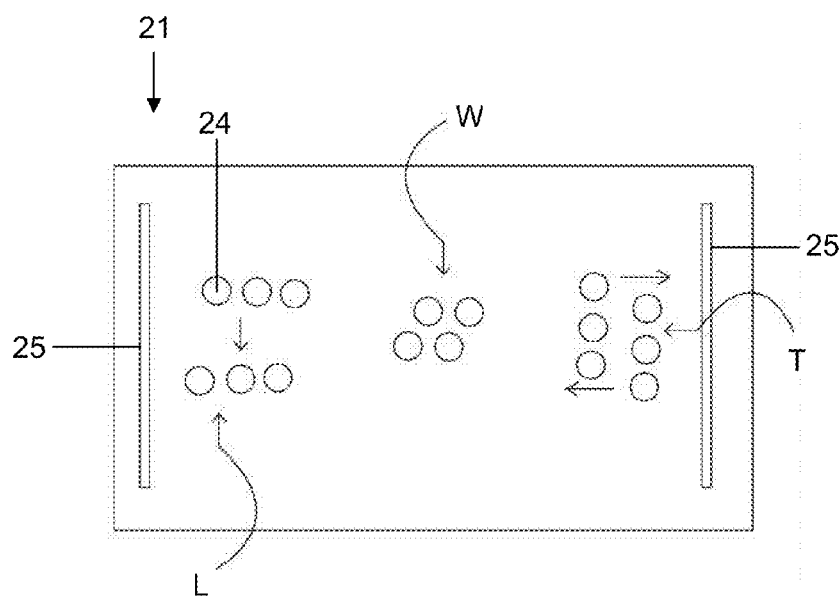

FIG. 3A shows the inspection assembly (20). The inspection assembly includes a carriage (21) that is fitted with a plurality of transducers for inspecting flaws in oil field tubulars. FIG. 3B shows one arrangement of the transducers on the inspection assembly. The transducers are of sufficient number and configuration to perform longitudinal, transverse, wall thickness, and oblique inspection techniques. The transducers are preferably of the type disclosed in U.S. Pat. No. 7,293,461 to Girndt (incorporated by reference herein), or alternatively, of another type known to those of skill in the art. The inspection assembly (20) includes longitudinal (22) and lateral (23) support members for supporting the carriage as it maneuvers the transducers into position to inspect tubulars (50). In this way, the longitudinal and lateral support members provide a support grid for indexing the carriage and transducers from one tubular to another as inspection progresses from tubular to tubular.

As shown in FIG. 3B, the inspection assembly (20) includes two infrared, or other sensors (25) for detecting the end of the tubulars (50). The sensor (25) communicates with a cylinder, which is functionally coupled to the inspection assembly (20). With input from sensor (25), the cylinder positions and reposition the carriage (21) over the tubulars, utilizing support members (22 and 23). The sensor (25) also detects and communicates the relative positioning of the transducers over each tubular if desired. In this way, a system control processor (not shown) may analyze the positioning data and flaw data to identify and characterize problems detected in the tubulars. The sensor is optional replaced or supplemented with manual controls such as visual input from a video camera or hand signals from a crew member.

A cat track assembly is optionally configured to move with or couple directly to the inspection assembly along rails 13, 14 as the inspection assembly travels. The cat track includes a power supply, electrical cables (such as e.g., coaxial cable) for pulsing the transducers, and other cables or transceivers for transmitting and receiving electrical signs with electrical components on the inspection assembly (e.g., sensors, video equipment). The cat track assembly is also preferably adapted to carry water used during the ultrasonic inspection. The cat track is the preferred embodiment for carrying equipment, materials and electronics that supports the inspection assembly, though equivalent structures are known to those of skill in the art.

In the preferred embodiment, two side-by-side pipe chutes are installed on each half of the inspection station (10) as shown in FIG. 1. Both side-by-side pipe chutes are loaded with tubulars at the same time. The inspection assembly (20) inspects the tubulars in sequence. For example, the inspection assembly begins in the "home position," which is the right end of the tubular in the second chute (11B), and ends at the right end of the tubular in the first chute (11A) after traversing the tubulars in each chute.

Figure 4:
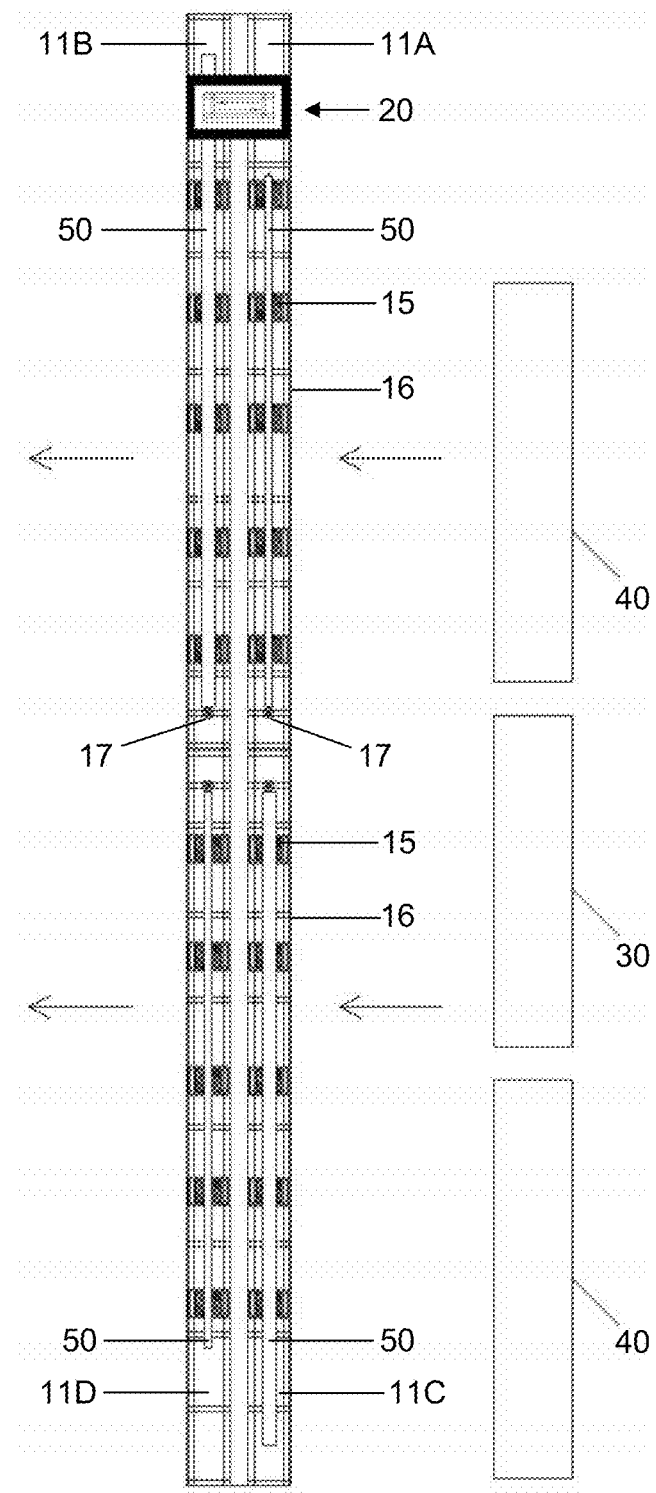
FIG. 4 is another example embodiment of the inspection station, including the walking beam.

FIG. 4 shows a walking beam (30) which positions the tubulars into the chutes (11) for inspection and removes them after inspection. A walking beam is generally known in the art for loading and unloading tubulars into and out of inspection apparatus or for other tube handling applications such as cooling bed for a pipe heat treat mill, among others. Tubulars awaiting inspection are stored in pipe feed rack (40), which is positioned adjacent to the inspection station. The walking beam (40) moves tubulars from the pipe feed rack (40) into and out of the chutes at a desired frequency.

Preferably, the inspection process starts by positioning the inspection assembly (20) at or near the home position. The walking beam (30) moves two tubulars (50) from the pipe feed rack (40) onto the inspection station—one tubular in first chute (11A), one tubular in second chute (11B). Rotators (15), which are functionally coupled to each chute (11A and 11B), spin the tubulars circumferentially about their longitudinal axis toward the center of the inspection station (10) and into contact with pipe stops (17). Now loaded, rotator (15) spins tubulars (50) within the chutes (11A, 11B) holding the tubulars against the pipe stops.

The inspection assembly (20) first inspects the tubular in chute (11B). The assembly (20) positions the carriage (21) over the tubular (50) in chute so that transducers (24) may inspect for flaws. Preferably, the transducers are positioned adjacent the tubular. From the home position, the inspection assembly (20) moves to the distal edge of the inspection station where chute (11B) terminates. The assembly (20) travels along the rails (13 and 14) as the transducers inspect the length of the spinning tubular in chute (11B), detecting flaws. When sensor (25) detects the end of the tubular in chute (11B), it signals the control processor that the inspection assembly has reached the end of the tubular and the inspection test head is lifted vertically away from the pipe just inspected. In turn, cylinder indexes the carriage (21) and transducers (24) into position over chute (11A) where the second tubular is spinning in place. Carriage (21) repositions the transducers (24) utilizing the longitudinal (22) and lateral support members (23) and cylinder. Thereafter, the inspection assembly returns toward the center of the inspection station (10) traveling along rails (13 and 14) and inspecting the tubular in chute (11A) as it goes. FIG. 4 shows the position of the inspection assembly after inspecting the tubular in chute (11B), before inspecting the tubular in chute (11A).

In its return trip, the inspection assembly (20) maintains the carriage (21) and transducers (24) and sets the test head down close enough to being inspecting the spinning tubular (50) in chute (11B) for flaws. The transducers (24) report flaw inspection data and the sensor (25) report positioning data as the inspection assembly (20) travels toward pipe stop (17). When sensor (25) detects the end of the second tubular (50), it signals the cylinder to raise the carriage, completing inspection of the tubular in chute (11B).

Next, the inspection assembly (20) begins inspection of tubulars loaded on the other side of the inspection station (10); that is, tubulars in chute (11C) and chute (11D). The inspection assembly first inspects the tubular loaded in chute (11C) travelling to the distal edge of the inspection assembly (10) along rails (13 and 14). The carriage and transducers index as needed to identify and characterize flaws. The inspection assembly then inspects tubulars loaded into chute (11D) returning to the home position. The sequence repeats as the inspection assembly (20) inspects tubulars newly loaded in chutes (11A and 11B). The inspection assembly optimally lowers and raises the transducers between tubulars as the inspection progresses.

For efficiency, the inspection assembly (20) inspects tubulars loaded on one half of the inspection station (10) while its other side is being loaded with new tubulars. For example, as above, the walking beam (30) loads tubulars from the pipe feed rack (40) into chutes (11C and 11D) when the inspection assembly (20) is conducting inspection of tubulars in chutes (11A and 11B). Once the inspection assembly (20) completes inspection of tubulars in chutes (11A and 11B), the assembly (20) moves to the other side of station (10) to inspect tubulars in chutes (11C and 11D) and the walking beam replaces tubulars in chutes (11A and 11B) with new tubulars to inspect. Optimally, the walking beam simultaneously offloads the tubulars that have been inspected from one or more chutes and replaces new tubulars to be inspected. In this manner, great numbers of tubulars may be loaded on the inspection station, inspected, and removed in short periods of time. Preferably, at all or most all times the transducers are in use with little or no down time.

In the preferred embodiment, the inspection process begins with tubulars loaded in all four chutes. The tubular in chute (11B) is inspected right to left then the inspection assembly (20) and transducers indexes over to chute (11A). When that tubular is inspected, the transducers are lifted up and moved the short distance to the left side of the tubular in chute (11C), which is already spinning at the rate needed for maximum productivity. When the transducer lifts from the tube/chute (11A) rotators (15) in chutes (11A) and (11B) start slowing their rotation and then stop. Then the walking beam (30), in one motion, lifts the two tubulars from chutes (11A) and (11B) while simultaneously loading two new tubulars into the chutes. The walking beam thus moves 4 tubulars with one operation. The inspection assembly (20) simultaneously inspects tubulars in chutes (11D) and (11C). By the time these two tubulars are inspected, the two new tubulars in chutes (11A) and (11B) will be rotating at inspection speed for the process to repeat.

Productivity Improvement

Known technology and mechanics used in inspecting oilfield tubulars consist of axial conveyor lines on both the inbound and outbound side that transfer the tube to be tested through a stationary rotating head as an example. Some systems are unable to begin inspection of the second pipe in the process until the pipe being inspected has completely cleared the inspection apparatus and rotating transducers. This is coupled with slippage when the second pipe is loaded onto the axial conveyor line.

Typical production figures for the existing technology is shown in the table below.

| Average Casing Pipe Length | Line Speed | Load Time (second) | Lost Productivity | Pipes Inspected Per Minute |
|---|---|---|---|---|
| 40 feet | 300 Feet/Min 5 Feet/Sec | 3 | 15 feet/sec | 2.7 |

Using the distance between subsequent tubes and above figures typical of the current technology, for every 3 tubes inspected a fourth tubular is lost as compared to the disclosed embodiments. The disclosed embodiments achieve greater output that the existing technology by (i) reducing the distance between tubulars being inspected (to the diameter of the pipe stop), and (ii) eliminating slippage.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition of matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

What is claimed:

1. An apparatus for inspecting a tubular comprising:
    at least one chute configured to receive a tubular;
    an inspection assembly configured to ultrasonically inspect a tubular in said chute;
    at least one rotator configured to apply a force on said tubular within said chute; and
    a pipe stop for applying a counter force on said tubular while said tubular is under said rotator force.

2. The apparatus of claim 1 wherein said inspection assembly is configured to ultrasonically inspect said tubular while said tubular is under a rotational force.

3. The apparatus of claim 1 where said inspection assembly is configured to ultrasonically inspect said tubular while said tubular is under a walking force.

4. The apparatus of claim 1 where said inspection assembly is configured to ultrasonically inspect said tubular while said tubular is under a walking force and a rotational force.

5. The apparatus of claim 1 further comprising a plurality of chutes configured to receive tubulars, a plurality of rotators configured to apply a force on said tubulars, and a plurality of pipe stops for applying a counter force on said tubulars while said tubulars are under a walking and/or said rotational force.

6. The apparatus of claim 5 wherein the combination of said counter force and said walking force or rotational force maintain said tubulars in said chutes.

7. The apparatus of claim 1 wherein said inspection assembly comprises one or more ultrasonic transducers configured to detect flaws in a tubular while said tubular is under a force applied by said rotator.

8. The apparatus of claim 1 wherein said inspection assembly is configured to pass over said chutes while inspecting tubulars loaded in said chute for flaws.

9. The apparatus of claim 1 further comprising a carriage for positioning and repositioning said inspection assembly relative to said tubular.

10. The apparatus of claim 9 wherein said inspection assembly further comprises a sensor operable to communicate with said carriage.

11. The apparatus of claim 10 wherein said sensor is operable to identify the position of a tubular and/or flaws in said tubular.

12. The apparatus of claim 11 wherein said sensor is operable to report the position of the inspection assembly, carriage, and/or tubular while said inspection assembly detects flaws in said tubular under said rotator force.

13. The apparatus of claim 1 wherein the combination of said counter force and said walking force and/or rotational force maintain said tubular in said chute.

14. A method for detecting flaws in oil field tubulars comprising:
   applying at least one force on said tubular to induce movement of said tubular; positioning an ultrasonic transducer relative to said tubular;
   traversing said ultrasonic transducers over said tubular while said tubular is under said force;
   inspecting said tubular for flaws while said tubular is under said at least one force; and
   reporting the position of any flaws detected in said tubular.

15. The method of claim 14 wherein said at least one force comprises a walking force and/or rotational force.

16. The method of claim 14 further comprising:
   placing said tubular in a chute;
   maintaining the position of said tubular in said chute through said force, wherein said force comprises at least one of a walking force and a rotational force.

17. The method of claim 14 wherein the reporting step comprises identifying the location of the end of a tubular in a first chute and the location of the end of a tubular in a second chute.

18. The method of claim 14 wherein the step of inspecting comprises indexing the position of an inspection assembly from a first chute to a second chute upon detecting the end of a tubular in said first chute.

* * * * *